United States Patent
Shin et al.

(10) Patent No.: US 9,637,509 B2
(45) Date of Patent: May 2, 2017

(54) LIGAND COMPOUND, CATALYST SYSTEM FOR OLEFIN OLIGOMERIZATION, AND METHOD FOR OLEFIN OLIGOMERIZATION USING THE SAME

(71) Applicant: LG CHEM, LTD., Seoul (KR)

(72) Inventors: Eun Ji Shin, Daejeon (KR); Yong Ho Lee, Daejeon (KR); Seok Pil Sa, Daejeon (KR); Ki Soo Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/896,608

(22) PCT Filed: Nov. 10, 2014

(86) PCT No.: PCT/KR2014/010744
§ 371 (c)(1),
(2) Date: Dec. 7, 2015

(87) PCT Pub. No.: WO2015/076520
PCT Pub. Date: May 28, 2015

(65) Prior Publication Data
US 2016/0207946 A1 Jul. 21, 2016

(30) Foreign Application Priority Data

Nov. 19, 2013 (KR) .................. 10-2013-0140873
Nov. 6, 2014 (KR) .................. 10-2014-0153906

(51) Int. Cl.
| | | |
|---|---|---|
| C07F 9/46 | (2006.01) |
| C08F 4/42 | (2006.01) |
| B01J 31/14 | (2006.01) |
| B01J 31/18 | (2006.01) |
| C07C 2/32 | (2006.01) |

(52) U.S. Cl.
CPC .............. *C07F 9/46* (2013.01); *B01J 31/143* (2013.01); *B01J 31/188* (2013.01); *C07C 2/32* (2013.01); *C08F 4/42* (2013.01); *B01J 2231/20* (2013.01); *B01J 2531/62* (2013.01); *C07C 2531/14* (2013.01); *C07C 2531/22* (2013.01)

(58) Field of Classification Search
CPC ......... C07F 9/46; C07C 2/32; C07C 2531/22; C07C 2531/14; B01J 31/188; B01J 31/143; B01J 2531/62; B01J 2231/20; C08F 4/42
USPC .......................................................... 564/12
See application file for complete search history.

(56) References Cited

U.S. PATENT DOCUMENTS

| | | | |
|---|---|---|---|
| 7,323,524 B2 | 1/2008 | Blann et al. | |
| 8,076,523 B2 | 12/2011 | Bollmann et al. | |
| 2011/0257350 A1 | 10/2011 | Jaber et al. | |
| 2012/0041241 A1 | 2/2012 | Ewart et al. | |
| 2012/0172645 A1* | 7/2012 | Sydora ................... B01J 31/143 585/511 |
| 2012/0316303 A1 | 12/2012 | Hanton et al. | |
| 2016/0271600 A1* | 9/2016 | Sa ......................... C07F 9/5727 |

FOREIGN PATENT DOCUMENTS

| | | |
|---|---|---|
| JP | 2006-511694 A | 4/2006 |
| JP | 2006-516265 A | 6/2006 |
| JP | 2006-517528 A | 7/2006 |
| JP | 2008-537905 A | 10/2008 |
| JP | 2009-516672 A | 4/2009 |
| KR | 10-2012-0098711 | 5/2012 |
| KR | 10-2012-0138309 A | 12/2012 |
| WO | 2004-056477 A1 | 7/2004 |
| WO | 2004-056479 A1 | 7/2004 |
| WO | 2005-123884 A2 | 12/2005 |
| WO | 2006-108803 A1 | 10/2006 |
| WO | 2007-057458 A1 | 5/2007 |
| WO | 2007-088329 A1 | 8/2007 |
| WO | 2008-004986 A1 | 1/2008 |
| WO | 2013-013300 A1 | 1/2013 |
| WO | 2013-168102 A1 | 11/2013 |
| WO | 2013-168106 A1 | 11/2013 |
| WO | 2013168103 A1 | 11/2013 |

OTHER PUBLICATIONS

MMAO ("Product Data Sheet for MMAO-3A / Heptane solutions" AkzoNobel, p. 1-2, dated Dec. 2014, downloaded from <http://www.pcpds.akzonobel.com/PolymerChemicalsPDS/showPDF.aspx?pds_id=430>).*
Belov ("Tetramerization of Ethylene to Octene-1 (A Review)" Petroleum Chemistry, 2012, vol. 52, No. 3, p. 139-154).*
Blann ("Ethylene tetramerisation: Subtle effects exhibited by N-substituted diphosphinoamine ligands" Journal of Catalysis 249 (2007) p. 244-249).*
Killian, E. et al., "The use of bis(diphenylphosphino)amines with N-aryl Functionalities in selective ethylene tri- and tetramerisation", J. Mol. Cat. A: Chemical, 2007, vol. 270, pp. 214-218; See abstract; paragraphs2.1-2.3; figures 2-3.
Sa, S. et al., "Chromium-based ethylene tetramerization with diphosphinoamines bearing pendent amine donors", J. Mol., Cat. A: Chemical, 2013, vol. 378, pp. 17-21 (May 24, 2013); See abstract, figure 1; paragraphs 2.3-2.4.
Cloete, N. et al., "Ethylee tri- and Tetramerization: a steric parameter selectivity switch form X-ray crystallograpy and computational analysis", Inorg. Chem 2013, vol. 52, pp. 2268-2270 (Feb. 8, 2013): See abstract; scheme 1.
Carter Anthea et al., "High activity ethylene trimerisation catalysts based on diphosphine ligands"; Received (in Cambridge, US) Feb. 8, 2002, Accepted Mar. 11, 2002; published Mar. 20, 2002.

(Continued)

Primary Examiner — Jafar Parsa
Assistant Examiner — Amy C Bonaparte
(74) Attorney, Agent, or Firm — Dentons US LLP

(57) ABSTRACT

Provided are ligand compounds selected from among N-(diphenylphosphino)-1,1-diphenyl-N-(4-phenylbutan-2-yl)phosphinamine and $N^4,N^4$-bis(diphenylphosphino)-$N^1,N^1$-diethylpentane-1,4-diamine, a catalyst system for olefin oligomerization, and a method for olefin oligomerization using the same. The catalyst system for olefin oligomerization has excellent catalytic activity, and yet, exhibits high selectivity to 1-hexene or 1-octene, thus enabling more efficient preparation of alpha-olefin.

8 Claims, No Drawings

(56) References Cited

OTHER PUBLICATIONS

Blann Kevin et al., "Ethylene Tetramerisation: Subtle effects exhibited by N-substituted diphosphinoamine ligands"; Received Jan. 8, 2007; revised Apr. 10, 2007; accepted Apr. 16, 2007; available online Jun. 11, 2007.
Jiang Tao et al., "Ethylene Tetramerization with a highly active and long-lifetime trinuclear diphenylphosphinoamine/Cr(III)/MAO catalyst"; Received Jun. 26, 2011; accepted Nov. 19, 2011; published online Mar. 12, 2012.
Bollman Annette et al., Ethylene Tetramerization: A New Route to Produce 1-Octene in Exceptionally High Selectivities; Received Jul. 22, 2004; published on web Oct. 20, 2004.
Kuhlmann Sven et al., N-substituted diphosphinoamines: Toward rational ligand design for the efficient tetramerizaiton of ethylene; Received Aug. 18, 2006; revised Oct. 12, 2006; accepted Oct. 13, 2006; Available online Nov. 28, 2006.
McDyre, L. E., et al., "A cw EPR and ENDOR investigation on a series of Cr(I) carbonyl complexes with relevance to alkene oligomerization catalysis: [Cr(CO)4L]+ (L=Ph2PN(R)PPh2, Ph2P(R)PPh2)†," Dalton Trans., 2010, 39, pp. 7792-7799.
Ghisolfi, A., et al., "Solvent-Dependent Reversible Ligand Exchange in Nickel Complexes of a Monosulfide Bis(diphenylphosphino)(N-thioether)amine," Chemistry—An Asian Journal, vol. 8(8), 2013, pp. 1795-1805.
Song, K., et al., "Synthesis, Structures, and Catalytic Ethylene Oligomerization Behaviors of Bis(phosphanyl) aminenickel(II) Complexes Containing N-Functionalized Pendant Groups," European Journal of Inorganic Chemistry, vol. 20, 2009, pp. 3016-3024.
Elowe, P. R., et al., "Nitrogen-Linked Diphosphine Ligands with Ethers Attached to Nitrogen for Chromium-Catalyzed Ethylene Tri- and Tetramerizations," Organometallics, vol. 25 (22), 2006, pp. 5255-5260.
Aydemir, M., et al., "Rhodium-catalyzed transfer hydrogenation with functionalized bis(phosphino)amine ligands," Inorganica Chimica Acta, vol. 398, 2013, pp. 1-10.
Vougioukalakis, G. C., et al., "Controlled Vinyl-Type Polymerization of Norbornene with a Nickel(II) Diphosphinoamine/Methylaluminoxane Catalytic System," Journal of Polymer Science, Part A: Polymer Chemistry, vol. 47(20), 2009, pp. 5241-5250.
RajanBabu, T. V., et al., "Heterodimerization of Olefins. 1. Hydrovinylation Reactions of Olefins That Are Amenable to Asymmetric Catalysis," Journal of Organic Chemistry vol. 68(22), 2003, pp. 8431-8446.
Song, Li-Cheng, et al., "Synthesis, Structural Characterization, and Electrochemical Properties of Dinuclear Ni/Mn Model Complexes for the Active Site of [NiFe]-Hydrogenases," Inorganic Chemistry, vol. 52(19), 2013, pp. 11618-11626.
Gallo, V., et al., "Chelating versus bridging bonding modes of N-substituted bis(diphenylphosphanyl)amine ligands in Pt complexes and Co2Pt clusters," Dalton Transactions, vol. 19, 2006, pp. 2342-2349.
Raghuraman, K., et al., "Half-sandwich cyclopentadienyl ruthenium complexes of achiral and chiral diphosphazanes†," Journal of the Chemical Society, Dalton Transactions, vol. 22, 2002, pp. 4289-4295.
Zhang, Q., et al., "Synthesis and coordination chemistry of aminophosphine derivatives of adenine †," The Royal Society of Chemistry, Dalton Transactions, 2003, pp. 3250-3257.

* cited by examiner

LIGAND COMPOUND, CATALYST SYSTEM FOR OLEFIN OLIGOMERIZATION, AND METHOD FOR OLEFIN OLIGOMERIZATION USING THE SAME

This application is a National Stage Entry of International Application No. PCT/KR2014/010744, filed Nov. 10, 2014, and claims the benefit of and priority to Korean Application Nos. 10-2013-0140873, filed Nov. 19, 2013 and 10-2014-0153906, filed Nov. 6, 2014, all of which are hereby incorporated by reference in their entirety for all purposes as if fully set forth herein.

TECHNICAL FIELD

The present invention relates to a ligand compound, a catalysts system for olefin oligomerization, and a method for olefin oligomerization using the same.

BACKGROUND OF ART

Linear alpha-olefins, which are important materials used as comonomers, cleaners, lubricants, plasticizers and the like, are commercially widely used, and particularly, 1-hexene and 1-octene are used a lot as comonomers for controlling the density of polyethylene when preparing linear low-density polyethylene (LLDPE).

In the existing preparation process of LLDPE, ethylene is copolymerized with alpha-olefin comononers, such as 1-hexene and 1-octene, so as to form branches in the polymer backbone to control the density.

Thus, there is a problem in that the cost of comonomers occupies a large part of production cost in the preparation of LLPDE having high comonomer content. There have been various attempts to solve the problem.

And, since alpha-olefins have various different application fields or market sizes according to the kind, a technology of selectively producing a specific olefin is commercially very important, and recently, a lot of studies are being progressed on the chromium catalyst technology for preparing 1-hexene or 1-octene with high selectivity through selective ethylene oligomerization.

The existing commercial preparation methods of 1-hexene or 1-octene include the SHOP process of Shell Chemical, the Ziegler process of Chevron Philips, and the like, whereby $C_{4-20}$ alpha-olefins with a wide distribution can be produced.

As a catalyst for trimerization of ethylene, a chromium-based catalyst using a ligand of the General Formula (R1)(R2)X—Y—X(R3)(R4) has been suggested. Wherein, X is phosphorous, arsenic or antimony, Y is a linking group such as —N(R5)—, and at least one of R1, R2, R3 and R4 has a polar or electron donating substituent.

And, as a ligand that exhibits catalytic activity to 1-hexene under catalytic conditions, studies have been progressed on (o-ethylphenyl)$_2$PN(Me)P(o-ethylphenyl)$_2$, which does not have a polar substituent on at least one of R1, R2, R3 and R4 (*Chem. Commun.*, 2002, 858).

However, regarding the above explained ligand containing a heteroatom of the prior art, there is continued demand for consistently continued multimerization activity and high selectivity when preparing 1-octene or 1-hexene.

PRIOR ART DOCUMENTS

Non-Patent Documents

1. *Chem. Commun.*, 2002, 858

DETAILED DESCRIPTION OF THE INVENTION

Technical Problem

The object of this invention is to provide a novel ligand compound that can oligomerize olefins with high catalytic activity and selectivity, a catalyst system for olefin oligomerization comprising the same, and a method for olefin oligomerization using the same.

Technical Solution

The present invention provides a ligand compound represented by the following Chemical Formula 1:

[Chemical Formula 1]

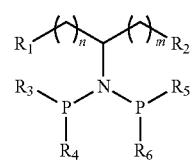

in the Chemical Formula 1,
at least one of $R_1$ and $R_2$ is a C3-20 branched alkyl group, a C1-20 linear or branched hydrocarbon group containing at least one heteroatom selected from N, O, F, S or P, a C6-40 aryl group, or a C3-30 heteroaryl group,
the other of $R_1$ and $R_2$ is hydrogen or a C1-20 linear or branched hydrocarbon group,
$R_3$ to $R_6$ are independently a C5-40 aryl group, and m and n are independently an integer of 0 to 10.

And, the present invention provides a catalyst system for olefin oligomerization, comprising the ligand compound; a source of transition metal; and a cocatalyst.

And, the present invention provides a method for olefin oligomerization, comprising the step of multimerizing olefins in the presence of the catalyst system for olefin oligomerization.

Hereinafter, a ligand compound, a catalyst system for olefin oligomerization, and a method for olefin oligomerization according to the present invention will be explained in detail.

According to one embodiment of the invention, provided is a ligand compound represented by the following Chemical Formula 1:

[Chemical Formula 1]

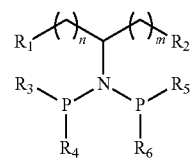

in the Chemical Formula 1,
at least one of $R_1$ and $R_2$ is a C3-20 branched alkyl group, a C1-20 linear or branched hydrocarbon group containing at least one heteroatom selected from N, O, F, S or P, a C6-40 aryl group, or a C3-30 heteroaryl group,
the other of $R_1$ and $R_2$ is hydrogen or a C1-20 linear or branched hydrocarbon group, $R_3$ to $R_6$ are independently a C5-40 aryl group, and m and n are independently n integer of 0 to 10.

The inventors newly synthesized a previously unknown ligand compound, confirmed through experiments that if a substituent introduced in the ligand compound is appropriately adjusted, an electronic/steric environment around a transition metal may be easily controlled, thus enabling olefin oligomerization with high catalytic activity and selectivity, and completed the invention.

Particularly, the ligand compound of the Chemical Formula 1 has a structure wherein bulky alkyl group, aryl group and the like are connected to a diphosphinoamine group, and it is characterized in that a steric in the vicinity of a metal center becomes large, thus controlling insertion of ethylene, to improve selectivity to 1-hexene and 1-octene.

Hereinafter, each substituent in the Chemical Formula 1 will be explained in detail.

The aryl group is preferably a C6-40 aromatic ring, and also includes an aromatic ring substituted with a C1-10 alkyl group. Specific examples of the aryl group include aromatic ring groups such as phenyl, naphthyl, anthracenyl, pyridyl, dimethylanilinyl, anisolyl, and the like, and the aromatic rings substituted with a C1-10 alkyl group, but are not limited thereto.

And, the heteroatom means N, O, F, S, or P, and the heteroaryl group means an aryl group containing at least one heteroatom.

And, the halogen group means fluorine(F), chlorine(Cl), bromine(Br), and iodine(I).

Wherein, at least one of $R_1$ and $R_2$ in the Chemical Formula 1 may be a C3-20 branched alkyl group, a C1-20 linear or branched hydrocarbon group containing at least one heteroatom selected from N, O, F, S or P, a C6-40 aryl group, or a C3-30 heteroaryl group. Specifically, the ligand compound of the Chemical Formula 1 is substituted with bulky alkyl group, aryl group, and the like on at least one of $R_1$ and $R_2$, and such a compound increases a steric in the vicinity of a metal center compared to a compound in which only non-bulky functional groups such as hydrogen, methyl, ethyl and the like are introduced at $R_1$ and $R_2$, thus enabling olefin oligomerization with high catalytic activity and selectivity.

In the Chemical Formula 1, at least one of $R_1$ and $R_2$ may be a C3-10 branched alkyl group, a C1-20 linear or branched hydrocarbon group containing at least one heteroatom selected from N, O, F, S or P, or a C6-20 aryl group.

And, the other of $R_1$ and $R_2$ may be a C1-10 linear or branched alkyl group, or a C6-20 aryl group.

And, representative examples of the ligand compound of the Chemical Formula 1 are as follows:

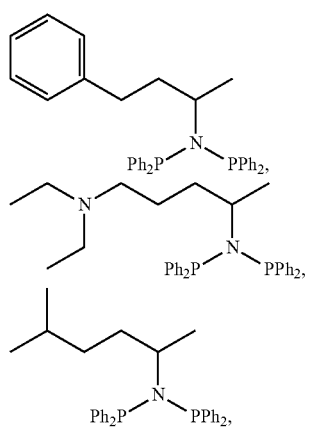

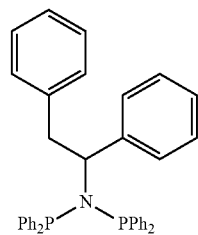

The compound represented by the Chemical Formula 1 includes all the possible optical isomers.

Meanwhile, the ligand compound represented by Chemical Formula 1 may be synthesized by the following Reaction Formula 1, but is not limited thereto. A method for preparing the compound represented by the Chemical Formula 1 will be explained in detail in the examples below.

[Reaction Formula 1]

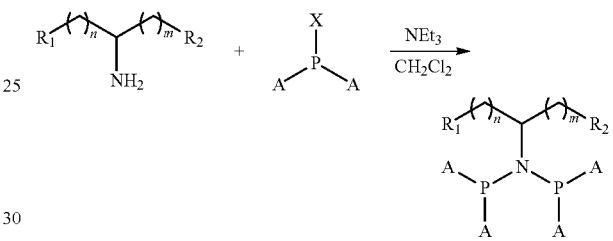

In the Reaction Formula 1, $R_1$ to $R_2$ are as defined in the Chemical Formula 1, A's are identical or different and independently are identical to the meanings of $R_3$ to $R_6$ in the Chemical Formula 1, and X is halogen.

Meanwhile, according to another embodiment, provided is a catalyst system for olefin oligomerization, comprising the ligand compound according to one embodiment, a source of transition metal and a cocatalyst.

As used herein, the term 'olefin oligomerization' means polymerization of a small number of olefins. When three olefins are polymerized, it is referred to as trimerization, when four olefins are polymerized, it is referred to as tetramerization, and the process of polymerization of a small number of olefins to form low molecular weight material is generally referred to as multimerization. Particularly, in the present invention, selective preparation of 1-hexene and 1-octene, main comonomers of LLDPE, from ethylene is referred to.

Selective olefin oligomerization is closely related to a catalyst system used. A catalyst system used for olefin oligomerization comprises a source of transition metal functioning as a main catalyst, and a cocatalyst, wherein the structure of the active catalyst may be changed according to the chemical structure of a ligand, thereby varying olefin selectivity.

As explained above, since the ligand compound according to one embodiment has a structure wherein bulky alkyl group, aryl group and the like are connected to a diphosphinoamine group, a catalyst system comprising the same may easily control the electrical/steric environment around a transition metal, thereby enabling olefin oligomerization with high catalytic activity and selectivity.

The source of transition metal functions as a main catalyst, and preferably, is at least one selected from the group consisting of chromium(III)acetylacetonate, tris(tetrahydrofuran)chromium trichloride, chromium(III)-2-ethylhexanoate, chromium(III)tris(2,2,6,6-tetramethyl-3,5-heptanedionate).

The cocatalyst is an organic metal compound including a Group 13 metal, and is not specifically limited as long as it can be used for olefin multimerization in the presence of a transition metal catalyst. Specifically, as the cocatalyst, at least one selected from the group consisting of the compounds represented by the following Chemical Formulae 2 to 4 may be used.

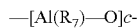  [Chemical Formula 2]

in the Chemical Formula 2, $R_7$'s are identical or different, and are independently a halogen radical, a C-20 hydrocarbyl radical, or a C1-20 hydrocarbyl radical substituted with halogen, and c is an integer of 2 or more,

  [Chemical Formula 3]

in the Chemical Formula 3,
D is aluminum or boron, $R_8$'s are identical or different, and are independently hydrogen, halogen, a C1-20 hydrocarbyl or a C1-20 hydrocaryl substituted with halogen,

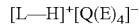  [Chemical Formula 4]

in the Chemical Formula 5,
L is neutral Lewis base, $[L-H]^+$ is Bronsted acid, Q is $Br^{3+}$ or $Al^{3+}$, and E's are independently a $C_{6-20}$ aryl group or a $C_{1-20}$ alkyl group, unsubstituted or substituted with at least one selected from the group consisting of halogen, $C_{1-20}$ hydrocarbyl, a $C_{1-20}$ alkoxy and phenoxy.

Examples of the compound represented by the Chemical Formula 2 may include modified methylaluminoxane(M-MAO), methylaluminoxane(MAO), ethylaluminoxane, isobutylaluminoxane, butylaluminoxane, and the like.

Examples of the alkyl metal compound represented by the Chemical Formula 3 may include trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tollylaluminum, dimethylaluminummethoxide, dimethylaluminumethoxide, trimethylboron, triethylboron, triisobutylboron, tripropylboron, tributylboron, and the like.

Examples of the compound represented by the Chemical Formula 4 may include triethylammonium tetraphenylboron, tributylammonium tetraphenylboron, trimethylammonium tetraphenylboron, tripropylammonium tetraphenylboron, trimethylammonium tetra(p-tollyl)boron, tripropylammonium tetra(p-tollyl)boron, triethylammonium tetra(o,p-dimethylphenyl)boron, trimethylammonium tetra(o,p-dimethylphenyl)boron, tributylammonium tetra(p-trifluoromethylphenyl)boron, trimethylammonium tetra(p-trifluoromethylphenyl)boron, tributylammonium tetrapentafluorophenylboron, N,N-diethylanilinium tetraphenylboron, N,N-diethylanilinium tetraphenylboron, N,N-diethylanilinium tetrapentafluorophenylboron, diethylammonium tetrapentafluorophenylboron, triphenylphosphonium tetraphenylboron, trimethylphosphonium tetraphenylboron, triethylammonium tetraphenylaluminum, tributylammonium tetraphenylaluminum, trimethylammonium tetraphenylaluminum, tripropylammonium tetraphenylaluminum, trimethylammonium tetra(p-tollyl)aluminum, tripropylammonium tetra(p-tollyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetraphenylaluminum, N,N-diethylanilinium tetrapentafluorophenylaluminum, diethylammonium tetrapentafluorophenylaluminum, triphenylphosphonium tetraphenylaluminum, trimethylphosphonium tetraphenylaluminum, triphenylcarbonium tetraphenylboron, triphenylcarbonium tetraphenylaluminum, triphenylcarbonium tetra(p-trifluoromethylphenyl)boron, triphenylcarbonium tetrapentafluorophenylboron, and the like.

As the cocatalyst of the catalyst system for olefin oligomerization, aluminoxane may be preferably used, and more preferably, methylaluminoxane(MAO) may be used.

The catalyst system for olefin oligomerization may have a mole ratio of the ligand compound:source of transition metal:cocatalyst of about 1:1:1 to about 10:1:10,000, preferably about 1:1:100 to about 5:1:3,000, so as to increase selectivity to linear alpha-olefin and multimerization activity, but is not limited thereto.

In the catalyst system for olefin oligomerization comprising the ligand compound represented by the Chemical Formula 1, a source of transition metal and cocatalyst, the three components may be added simultaneously or sequentially in a random order in a suitable solvent in the absence or presence of monomers, and be obtained as an active catalyst. The active solvent may include heptanes, toluene, cyclohexane, methylcyclohexane, 1-hexene, diethylether, tetrahydrofuran, acetonitrile, dichloromethane, chloroform, chlorobenzene, methanol, acetone and the like, but is not limited thereto.

Meanwhile, according to still another embodiment of the invention, provided is a method for olefin oligomerization, comprising the step of multimerizing olefins in the presence of the catalyst system for olefin oligomerization. If the catalyst system for olefin oligomerizatoin according to the present invention is used, a method for olefin oligomerization with improved activity and selectivity may be provided. The olefin may be preferably ethylene.

The olefin oligomerization according to the present invention may be conducted as a homogeneous liquid phase reaction, a slurry reaction wherein a catalyst system is not dissolved in part or in whole, a two-phase liquid/liquid reaction, or a bulk phase reaction or a gas phase reaction wherein product olefin acts as a main medium, in the absence or presence of an inert solvent, using the catalyst system for olefin oligomerization and a common device and contact technology, and the homogeneous liquid phase reaction is preferable.

The olefin oligomerization may be conducted in any inert solvent that does not react with a catalyst compound and an activator. The suitable inert solvent may include benzene, toluene, xylene, cumene, heptanes, cyclohexane, methylcyclohexane, methylcyclopentane, hexane, pentane, butane, isobutane and the like, but is not limited thereto. Wherein, the solvent may be treated with a small amount of alkylaluminum to remove a small amount of water or air acting as a catalyst poison, before use.

The olefin oligomerization may be conducted at a temperature of about 5° C. to about 200° C., preferably about 30° C. to about 150° C. And, the olefin oligomerization may be conducted at a pressure of about 1 bar to about 300 bar, preferably about 2 bar to about 150 bar.

According to one example of the invention, it was confirmed that as a result of oligomerizing ethylene with a catalyst system using the ligand compound represented by the Chemical Formula 1 as a ligand, 1-hexene and 1-octene can be selectively synthesized.

Advantageous Effects

By using a catalyst system comprising the ligand compound according to the present invention, ethylene may be oligomerized with higher catalytic activity and selectivity compared to the existing catalyst system.

DETAILED DESCRIPTION OF THE EMBODIMENTS

Hereinafter, the present invention will be explained in detail with reference to the following examples. However, these examples are only to illustrate the invention and the scope of the invention is not limited thereto.

<Synthesis of Ligand Compound>

SYNTHESIS EXAMPLE

All the reactions were progressed using Schlenk technique or a Glove box under argon atmosphere. The synthesized compounds were analyzed by $^1$H(500 MHz) and $^{31}$P(202 MHz) NMR spectra using a Varian 500 MHz spectrometer. Shift was expressed in ppm, downfield from TMS, with a residual solvent peak as a reference. A phosphorous probe was calibrated with aqueous $H_3PO_4$. Under argon atmosphere, amine (10 mmol) and triethylamine (3~10 equiv. to amine) were dissolved in dichloromethane (80 mL). While the flaks was immersed in a water bath, chlorodiphenylphosphine(20 mmol) was slowly introduced, and the mixture was stirred overnight. The solvent was removed under vacuum, and then, another solvent (diethyl ether, tetrahydrofuran or hexane) was introduced, the mixture was sufficiently stirred, and triethylammoniumchloride salt was removed with an air-free glass filter. The solvent was removed in the filtrate to obtain a product. Starting amines for preparing ligands used in each Example and Comparative Example are shown in the following Table 1.

TABLE 1

| Synthesis Example | Starting amine | Ligand |
|---|---|---|
| Synthesis Example 1 | 2-amino-4-phenylbutane | (structure with Ph$_2$P–N–PPh$_2$ bearing phenylbutyl group) |
| Synthesis Example 2 | 4-Amino-1-diethylaminopentane | (structure with Ph$_2$P–N–PPh$_2$ and diethylamino chain) |
| Synthesis Example 3 | 1,2-diphenylethylamine | (structure with Ph$_2$P–N–PPh$_2$ bearing 1,2-diphenylethyl group) |

TABLE 1-continued

| Synthesis Example | Starting amine | Ligand |
|---|---|---|
| Comparative Synthesis Example 1 | 2-aminopropane | (structure with Ph$_2$P–N–PPh$_2$ bearing isopropyl group) |
| Comparative Synthesis Example 2 | 3-aminopentane | (structure with Ph$_2$P–N–PPh$_2$ bearing 3-pentyl group) |
| Comparative Synthesis Example 3 | 2-amino-1-diethylaminopropane | (structure with two N–PPh$_2$ groups on diethylamino-propane) |

<Ethylene Oligomerization>

Example 1

Under argon gas, Cr(acac)$_3$ (17.5 mg, 0.05 mmol) and the ligand prepared in the Synthesis Example 1 (0.1 mmol) were put in a flask, toluene (10 mL) was added, and the mixture was stirred to prepare a 5 mM solution.

A 600 mL Parr reactor was prepared, vacuum was applied at 120° C. for 2 hours, and then, the temperature was decreased to 45° C., and the inside was replaced with argon. Cyclohexane (270 g) and 2 mL of MAO (10 wt % toluene solution, Al/Cr=300) were introduced, and 2 mL of the 5 mM solution(10 umol) was introduced in the reactor. The mixture was stirred at 500 rpm for 2 minutes, and then, a valve of an ethylene line adjusted to 45 bar was opened to fill the inside of the reactor with ethylene, and the mixture was stirred at 500 rpm for 15 minutes. The ethylene line valve was closed, the temperature was adjusted to 0° C., the reactor was cooled with an ice/acetone bath, and then, non-reacted ethylene was slowly vented, and 0.5 mL of nonane (GC internal standard) was put. Thereafter, 2 mL of the liquid part of the reactor was taken and quenched with water, and the organic part was filtered with a PTFE syringe filter to make a GC sample. The GC sample was analyzed with GC. To the remaining reaction solution, 400 mL of ethanol/HCl (10 vol %) was added, and the mixture was stirred and filtered to obtain polymer. The obtained polymer was dried overnight in a 65° C. vacuum oven.

Example 2

A reaction was conducted by the same method as Example 1, except using 1 ml (5 umol) of the catalyst 5 mM solution.

Example 3

A reaction was conducted by the same method as Example 1, except using the ligand prepared in Synthesis Example 2.

Example 4

A reaction was conducted by the same method as Example 2, except using the ligand prepared in Synthesis Example 2.

Example 5

A reaction was conducted by the same method as Example 1, except using the ligand prepared in Synthesis Example 3.

Comparative Example 1

Under argon gas, Cr(acac)₃ (17.5 mg, 0.05 mmol) and the ligand prepared in the Comparative Synthesis Example (0.1 mmol) were put in a flask, toluene (10 mL) was added, and the mixture was stirred to prepare a 5 mM solution.

A 600 mL Parr reactor was prepared, vacuum was applied at 120° C. for 2 hours, and then, the temperature was decreased to 45° C., and the inside was replaced with argon. And then, 300 g of toluene and 2 mL of MAO (10 wt % toluene solution, Al/Cr=300) were introduced, and 2 mL of the 5 mM solution (10 umol) was introduced in the reactor. The mixture was stirred at 500 rpm for 2 minutes, and then, a valve of an ethylene line adjusted to 45 bar was opened to fill the inside of the reactor with ethylene, and the mixture was stirred at 500 rpm for 30 minutes. The ethylene line valve was closed, the temperature was adjusted to 0° C., the reactor was cooled with an ice/acetone bath, and then, non-reacted ethylene was slowly vented, and 0.5 mL of nonane(GC internal standard) was put. Thereafter, 2 mL of the liquid part of the reactor was taken and quenched with water, and the organic part was filtered with a PTFE syringe filter to make a GC sample. The GC sample was analyzed with GC. To the remaining reaction solution, 400 mL of ethanol/HCl (10 vol %) was added, and the mixture was stirred and filtered to obtain polymer. The obtained polymer was dried overnight in a 65° C. vacuum oven.

Comparative Example 2

A reaction was conducted by the same method as Comparative Example 1, except using a ligand prepared in Comparative Synthesis Example 2, and using 1 ml (5 umol) of the catalyst 5 mM solution.

Comparative Example 3

A reaction was conducted by the same method as Comparative Example 1, except using a ligand prepared in Comparative Synthesis Example 3.

The results of Examples 1 to 5 and Comparative Examples 1 to 3 are shown in the following Table 2.

TABLE 2

| | Activity (kg/mol/Cr/hr) | Selectivity (wt %) | | | Solid PE (wt %) |
|---|---|---|---|---|---|
| | | 1-hexene | 1-octene | Sum | |
| Comparative Example 1 | 5182 | 14.4 | 69.6 | 84.0 | 1.1 |
| Comparative Example 2 | 10269 | 14.0 | 70.1 | 84.1 | 0.11 |
| Comparative Example 3 | 1600 | 9.9 | 36.5 | 46.4 | 2.3 |
| Example 1 | 14177 | 17.5 | 69.1 | 86.6 | 0.53 |
| Example 2 | 11280 | 15.8 | 70.3 | 86.1 | 0.85 |
| Example 3 | 8111 | 20.6 | 66.6 | 87.2 | 0.53 |
| Example 4 | 12603 | 15.2 | 70.1 | 85.3 | 0.18 |
| Example 5 | 6017 | 19.6 | 67.2 | 86.8 | 0.80 |

From the results of the Table 2, it can be seen that in the case of Examples, compared to Comparative Examples, very high multimerization activity is exhibited, selectivity to 1-hexene and 1-octene is remarkably improved, and the amount of by-product, solid PE is small.

The invention claimed is:

1. A ligand compound selected from the group consisting of:

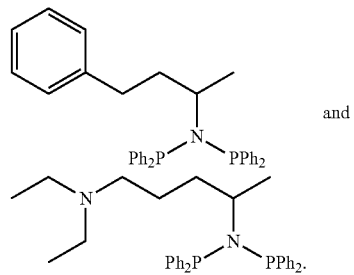

and

2. A catalyst system for olefin oligomerization, comprising the ligand compound according to claim 1, a source of transition metal and a cocatalyst.

3. The catalyst system according to claim 2, wherein the source of transition metal is at least one selected from the group consisting of chromium(III)acetylacetonate, tris(tetrahydrofuran)chromium trichloride, chromium(III)-2-ethylhexanoate, and chromium(III)tris(2,2,6,6-tetramethyl-3,5-heptanedionate).

4. The catalyst system according to claim 2, wherein the cocatalyst is at least one selected from the group consisting of the compounds of Chemical Formulae 2, 3 and 4:

$$-[\text{Al}(R_7)-O]c- \quad \text{[Chemical Formula 2]}$$

wherein in the Chemical Formula 2, each $R_7$ is identical or different, and are independently a halogen radical, a C1-20 hydrocarbyl radical, or a C1-20 hydrocarbyl radical substituted with halogen, and c is an integer of 2 or more, $$D(R_8)_3 \quad \text{[Chemical Formula 3]}$$

wherein in the Chemical Formula 3, D is aluminum or boron, each $R^8$ is identical or different, and are independently hydrogen, halogen, a C1-20 hydrocarbyl or a C1-20 hydrocaryl substituted with halogen, $$[L-H]^+[Q(E)_4]^- \quad \text{[Chemical Formula 4]}$$

wherein in the Chemical Formula 4, L is a neutral Lewis base, $[L-H]^+$ is a Bronsted acid, Q is $B^{3+}$ or $Al^{3+}$, and E is independently a $C_{6-20}$ aryl group or a $C_{1-20}$ alkyl group, unsubstituted or substituted with at least one group selected from the group consisting of halogen, $C_{1-20}$ hydrocarbyl, a $C_{1-20}$ alkoxy and phenoxy.

5. A method for olefin oligomerization, comprising the step of multimerizing olefins in the presence of the catalyst system for olefin oligomerization of claim 2.

6. The method for olefin oligomerization according to claim 5, wherein the olefin is ethylene.

7. The method for olefin oligomerization according to claim 5, wherein the multimerization temperature is 5 to 200° C.

8. The method for olefin oligomerization according to claim 5, wherein the multimerization pressure is 1 to 300 bar.

* * * * *